US005633266A

United States Patent [19]

Baker et al.

[11] Patent Number: 5,633,266

[45] **Date of Patent: *May 27, 1997**

[54] AZACYCLIC COMPOUNDS COMPOSITIONS CONTAINING THEM AND THEIR USE AS TACHYKININ ANTAGONISTS

[75] Inventors: Raymond Baker; Christopher J. Swain; Brian J. Williams, all of Harlow, United Kingdom

[73] Assignee: Merck Sharp & Dohme Ltd., Hoddesdon, England

[ * ] Notice: The term of this patent shall not extend beyond the expiration date of Pat. No. 5,496,833.

[21] Appl. No.: 495,429

[22] PCT Filed: Feb. 10, 1994

[86] PCT No.: PCT/EP94/00412

§ 371 Date: Jul. 26, 1995

§ 102(e) Date: Jul. 26, 1995

[87] PCT Pub. No.: WO94/19323

PCT Pub. Date: Sep. 1, 1994

[30] Foreign Application Priority Data

Feb. 18, 1993 [GB] United Kingdom .................... 9303243
Oct. 27, 1993 [GB] United Kingdom .................... 9322150

[51] Int. Cl.$^6$ ........................ A61K 31/445; C07D 211/42

[52] U.S. Cl. .......................... 514/327; 514/326; 546/210; 546/216

[58] Field of Search .................................... 544/239, 240, 544/241, 405; 546/153, 157, 167, 213, 200, 210, 209, 194, 214, 205, 206, 216, 219, 220, 221, 208, 198, 196, 202, 201; 514/326, 327

[56] References Cited

U.S. PATENT DOCUMENTS

| | | | |
|---|---|---|---|
| 5,444,074 | 8/1995 | Baker et al. | 514/326 |
| 5,459,270 | 10/1995 | Williams et al. | 546/152 |
| 5,496,833 | 3/1996 | Baker et al. | 514/326 |

FOREIGN PATENT DOCUMENTS

| | | |
|---|---|---|
| 0035743 | 9/1981 | European Pat. Off. . |
| 0436334 | 7/1991 | European Pat. Off. . |
| 0499313 | 8/1992 | European Pat. Off. . |
| 0528495 | 2/1993 | European Pat. Off. . |
| WO93/21181 | 10/1993 | WIPO . |

*Primary Examiner*—C. Warren Ivy
*Assistant Examiner*—Garth M. Dahlen
*Attorney, Agent, or Firm*—J. Eric Thies; David L. Rose

[57] ABSTRACT

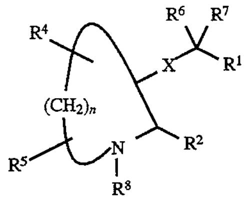

(I)

The present invention relates to compounds of formula (I), and salts and prodrugs thereof, wherein n is 1 , 2 or 3 and where any carbon atom of $(CH_2)_n$ may be substituted by $R^4$ and/or $R^5$; X represents O or S; $R^1$ represents optionally substituted $(CH_2)_q$phenyl, wherein q is 0, 1, 2 or 3; $R^2$ represents optionally substituted aryl, heteroaryl, benzhydryl or benzyl; $R^4$ and $R^5$ each independently represent H, halo, $C_{1-6}$alkyl, oxo, $CO_2R^a$ or $CONR^aR^b$; $R^6$ represents H or $C_{1-6}$alkyl; $R^7$ represents $C_{1-6}$alkyl or optionally substituted phenyl; $R^8$ represents H, $COR^a$, $CO_2R^a$, $CONR^aR^b$, $COCO_2R^a$, $C_{1-6}$alkyl optionally substituted by a variety of substituents, or $C_{1-6}$alkyl, optionally substituted by oxo, substituted by an optionally substituted aromatic heterocycle. The compounds are tachykinin antagonists useful for treating pain or inflammation, migraine or emesis.

17 Claims, No Drawings

AZACYCLIC COMPOUNDS COMPOSITIONS CONTAINING THEM AND THEIR USE AS TACHYKININ ANTAGONISTS

The present application is a National Phase application under 35 U.S.C. §371 of PCT Application No. PCT/EP94/0412, filed Feb. 10, 1994.

This invention relates to a class of azacyclic compounds, which are useful as tachykinin antagonists. More particularly, the compounds of the invention comprise an azacyclic ring system substituted by an arylmethyloxy or arylmethylthio moiety.

The tachykinins are a group of naturally-occurring peptides found widely distributed throughout mammalian tissues, both within the central nervous system and in the peripheral nervous and circulatory systems. The three known mammalian tachykinins are as follows:

Substance P therefor

Nedrokinin A therefor

Neurokinin B therefor

For example, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (Dec. 1987) 8 506–510], specifically in the transmission of pain in migraine (B. E. B. Sandberg et al, J. Med Chem, (1982) 25 1009) and in arthritis [Levine et al in Science (1984) 226 547–549]. These peptides have also been implicated in gastrointestinal (GI) disorders and diseases of the GI tract such as inflammatory bowel disease [Mantyh et. al in Neuroscience (1988) 25 (3) 817–37 and D. Regoli in "Trends in Cluster Headache" Ed. Sicuteri et al Elsevier Scientific Publishers, Amsterdam (1987) page 85)] and emesis [F. D. Tattersall et. al., Eur. J. Pharmacel., (1993) 250, R5–R6]. It is also hypothesised that there is a neurogenic mechanism for arthritis in which substance P may play a role [Kidd et al "A Neurogenic Mechanism for Symmetrical Arthritis" in The Lancet, 11 Nov. 1989 and Grönblad et al "Neuropeptides in Synovium of Patients with Rheumatoid Arthritis and Osteoarthritis" in J. Rheumatol. (1988) 15(12) 1807–10]. Therefore, substance P is believed to be involved in the inflammatory response in diseases such as rheumatoid arthritis and-osteoarthritis [O'Byrne et al in Arthritis and Rheumatism (1990) 33 1023–8]. Other disease areas where tachykinin. antagonists are believed to be useful are allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9] vasodilation, bronchospasm, reflex or neuronal control of the viscera [Mantyh et al, PNAS (1988) B5 3235–9]and, possibly by arresting or slowing β-amyloid-mediated neurodegenerative changes [Yankner et El Science, (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et. al., Cancer Research (1992) 52, 4554–7].

Substance P may also play a role in demyelinating diseases such as multiple sclerosis and amyotrophic lateral sclerosis [J. Luber-Narod et. al., poster presented at C.I.N.P. XVIIIth Congress, 28th Jun.–2nd Jul., 1992], and in disorders of bladder function such as bladder detrusor hyperreflexia (Lancet, 16th May, 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent specification no. 0 436 334), ophthalmic disease such as conjuctivitis, vernal conjunctivitis.. and the like, and cutaneous diseases such as contact dermatitis, atropic dermatitis, urticaria, and other eczematoid dermatitis (European patent specification no. 0 394 989).

In view of their metabolic instability, peptide derivatives are likely to be of limited utility as therapeutic.agents. It is for this reason that non-peptide tachykinin antagonists are sought.

In essence, this invention provides a class of potent non-peptide tachykinin antagonists. By virtue of their non-peptide nature, the compounds of the present invention do not suffer from the shortcomings, in terms of metabolic instability, of the known peptide-based tachykinin antagonists discussed above.

The present invention provides a compound of formula (I), or a salt or prodrug thereof:

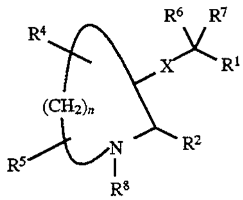

(I)

wherein n is 1, 2 or 3 and where any carbon atom of $(CH_2)_n$ may be substituted by $R^4$ and/or $R^5$;

X represents O or S;

$R^1$ represents $(CH_2)_q$phenyl, wherein q is 0, 1, 2 or 3, which may be optionally substituted in the phenyl ring by 1, 2 or 3 groups selected from $C_{1-6}$alkyl, $C_{2-6}$ alkenyl, $C_{2-6}$alkynl, halo, cyano, nitro, triluoromethyl, trimethylsilyl, —$OR^a$, $SR^a$, $SOR^a$, $SO_2R^a$, —$NR^aR^b$, —$NR^aCOR^b$, —$NR^aCO_2R^b$, —$CO_2R^a$ and COLN-$R^aR^b$;

$R^2$ represents aryl selected from phenyl and naphthyl; heteroaryl selected from indazolyl, thienyl, furyl, pyridyl, thiazolyl, tetrazolyl and quinolyl; benzhydryl; or benzyl; wherein each aryl or heteroaryl moiety may be substituted by $C_{1-6}$alkyl, $C_{1-6}$alkoxy, halo or trifluoromethyl;

$R^4$ and $R^5$ each independently represent H, halo, $C_{1-6}$alkyl, oxo, $CO_2R^a$ or $CONR^aR^b$;

$R^6$ represents H or $C_{1-6}$alkyl;

$R^7$ represents $C_{1-6}$alkyl or phenyl optionally substituted by 1, 2 or 3 groups selected from $C_{1-6}$alkyl, $C_{2-6}$alkenyl, $C_{2-6}$alkynyl, halo, cyano, nitro, trifluoromethyl, trimethylsilyl, —$OR^a$, $SR^a$, $SOR^a$, $SO_2R^a$, —$NR^aR^b$, —$NR^aCOR^b$, —$NR^aCO_2R^b$, —$CO_2R^a$ and —$CONR^aR^b$;

$R^8$ represents H, $COR^a$, $CO_2R^aCOCONR^aR^b$, $COCO_2R^a$, $C_{1-6}$alkyl optionally substituted by a group selected from ($CO_2R^a$, $CONR^aR^b$, hydroxy, cyano, $COR^a$, $NR^aR^b$, $C(NOH)NR^aR^b$, CONHphenyl($C_{1-4}$alkyl) $COCO_2R^a$, $CONHNR^aR^b$, C(S) $NR^aR^b$, $CONR^aC_{1-6}alkylR^{12}$, $CONR^{13}C_{2-6}$alkynyl, $CONR^{13}C_{2-6}$alkenyl, $COCONR^aR^b$, $CONR^aC(NR^b)NR^aR^b$, $CONR^a$heteroaryl, and phenyl optionally substituted by one or more substituents selected from $C_{1-6}$alkyl, $C_{1-6}$alkoxy, halo and trifluoromethyl) or $C_{1-6}$alkyl, optionally substituted by Oxo, substituted by an optionally substituted aromatic heterocycle;

$R^a$ and $R^b$ each independently represent H, $C_{1-6}$alkyl, trifluoromethyl or phenyl optionally substituted by $C_{1-6}$alkyl, halo or trifluoromethyl;

$R^{12}$ represents $OR^a$, $CONR^aR^b$ or heteroaryl; and $R^{13}$ represents H or $C_{1-6}$alkyl.

As used herein, the definition of each expression, when it occurs more than once in any structure, is intended to be independent of its definition elsewhere in the same structure.

The alkyl, alkenyl and alkynyl groups referred to with respect to the above formula may represent straight, branched or cyclic groups. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

The present invention includes within its scope prodrugs of the compounds of formula (I) above. In, general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs" ed H. Bundgaard, Elsevier, 1985.

The compounds according to the invention may exist both as enantiomers and as diastereomers. In particular, the relative orientation of the 2- and 3-substituents on the azacyclic ring may give rise to cis and trans diastereoisomers, of which the cis stereochemistry is preferred. It is to be understood that all such isomers and mixtures thereof are encompassed within the scope of the present invention.

Preferably n is 2 or 3, more preferably 3.

Preferably X represents O.

Preferably q is O and $R^1$ represents substituted phehyl. When $R^1$ is substituted phenyl suitable substituents include nitro, trifluoromethyl, trimethylsily, bromo, chloro, fluoro, iodo, cyano, methyl, ethyl, cyclopropyl, vinyl, methoxy, phenoxy, amino and carbonylmethoxy. Preferably $R^1$ represents phenyl substituted by one or more groups selected from methyl, trifluoromethyl, chloro and t-butyl.

Preferably $R^1$ represents disubstituted phenyl, more preferably 3,5-disubstituted phenyl such as 3,5-dichlorophenyl or 3,5-bis(trifluoromethyl)phenyl, or monosubstituted phenyl, such as 3-substituted phenyl, e.g. 3-t-butylphenyl.

Preferably $R^2$ represents unsubstituted benzhydryl, phenyl substituted by halo such as chloro, for example 4-chlorophenyl, or unsubstituted phenyl, more preferably unsubstituted phenyl.

Preferably $R^4$ and $R^5$ both represent H.

Suitable values for $R^6$ include H, methyl and ethyl. Preferably $R^6$ represents H or methyl, more preferably H.

Preferably $R^7$ represents $C_{1-6}$alkyl, such as methyl or ethyl, more preferably methyl.

When $R^8$ represents $C_{1-6}$alkyl, optionally substituted by oxo, substituted by a substituted aromatic heterocycle, suitable substituents in the heterocyclic ring include $C_{1-6}$alkyl, $C_{1-6}$alkoxy, oxo, thioxo, halo, trifluoromethyl, $NR^aR^b$, $NR^aCOR^b$, $CONR^aR^b$, $CO_2R^a$, $SO_2R^a$ and $CH_2OR^a$, where $R^a$ and $R^b$are as previously defined.

Preferably $R^8$ represents $C_{1-3}$alkyl such as methyl, ethyl or i-propyl substituted by a substituted or unsubstituted aromatic heterocycle. Suitable heterocycles include thienyl, furyl, pyrrolyl, pyridyl, pyrazolyl, triazolyl, tetrazolyl, thiazolyl, pyrazinyl, pyridazinyl, oxazolyl, oxadiazolyl, thiadiazolyl, isoxazolyl, quinolyl, isothiazolyl, imidazolyl, benzimidazolyl, benzoxazolyl, benzothiophenyl, benzofuranyl and indolyl.

In one group of compounds according to the invention $R^8$ represents $CH_2$-Het, $CH(CH_3)$-Het, $C(CH_3)_2$-Het or C(O)-Het, where Het is pyrrolyl, pyrazolyl, pyrazinyl, pyridazinyl, oxadiazolyl, thiadiazolyl, imidazolyl, benzimidazolyl, benzoxazolyl, benzothiophenyl, benzofuranyl or indolyl.

Preferably $R^8$ represents $CH_2$-Het,$CH(CH_3)$-Het, $C(CH_3)_2$-Het or C(O)-Het where Het is substituted or unsubstituted oxazolyl, oxadiazolyl, tetrazolyl, thiazolyl, thiadiazolyl, furanyl, thienyl, triazolyl, pyrazinyl, pyridyl, pyridazinyl, imidazolyl or benzimidazolyl. More preferably Het is triazolyl or triazolyl substituted by oxo.

Other suitable values for $R^8$ include H, $COR^a$, $CO_2R^a$, $COCONR^aR^2$, $COCO_2R^a$, $C_{1-6}$alkyl and $C_{1-6}$alkyl substituted by a group selected from $CO_2R^a$, $CONR^aR^b$, CN, $C(NOH)NR^aR^b$, CONHphenyl($C_{1-4}$alkyl), optionally substituted phenyl, $CONHNR^aR^b$, $COCONR^aR^b$, $CONR^aC(NH)NH_2$, $CSNR^aR^b$, $CONR^{13}C_{2-6}$alkynyl, $CONR^aC_{1-6}alkylR^{12}$ and $CONR^a$heteroaryl.

It will be appreciated that, when $R^8$ comprises a heteroaryl moiety substituted by an oxo or thioxo substituent, different tautomeric forms are possible so that the substituent on the heteroaryl moiety may be represented as =O or —OH, or =S or —SH, respectively. For the avoidance of doubt, all such tautomeric forms are embraced by the present invention.

A particular sub-class of compounds according to the invention is represented by compounds of formula (Ia), and salts and prodrugs thereof:

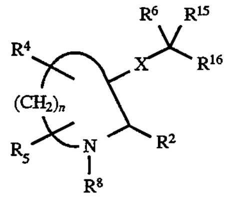
(Ia)

wherein $R^2$, $R^4$, $R^5$, $R^6$, $R^8$, X and n are as defined for formula (I) above;

$R^{15}$ represents $C_{1-6}$alkyl; and $R^{16}$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, $—OR^a$, $SR^a$, $SOR^a$, $SO_2R^a$, $—NR^aR^b$, $—NR^aCOR^b$, $—NR^aCO_2R^b$, $—CO_2R^a$ and $—CONR^aR^b$.

A further sub-class of compounds according to the invention is represented by compounds of formula (Ib) and salts and prodrugs thereof:

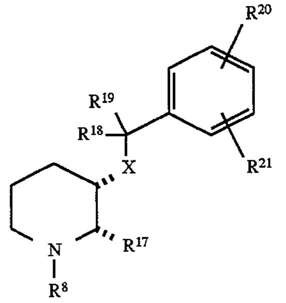

(Ib)

wherein

X represents 0 or S, preferably O;

$R^8$ is as defined for formula (I);

$R^{17}$ represents phenyl or benzhydryl wherein any of the phenyl rings of the phenyl or benzhydryl moieties may optionally be substituted by halo or trifluoromethyl, preferably unsubstituted phenyl;

$R^{18}$ is methyl;

$R^{19}$ is H or methyl; and $R^{20}$ and $R^{21}$ independently represent H $C_{1-6}$alkyl, $C_{2-6}$alkenyl, $C_{2-6}$alkynyl, chloro, bromo, fluoro, iodo, cyano, nitro, trifluoromethyl, trimethylsilyl $OR^a$, $SR^a$ $SOR^a$, $SO_2R^a$, $NR^aR^b$, $NR^aCOR^b$, $NR^aCO_2R^b$, $CO_2R^a$ or $CONR^aR^b$, where $R^a$ and $R^b$ are as previously defined.

Particular values of $R^{20}$ and $R^{21}$ include methyl, ethyl, t-butyl, chloro and trifluoromethyl. Preferably $R^{20}$ and $R^{21}$ are both other than hydrogen and are located at the 3- and 5-positions of the phenyl ring.

A preferred group of compounds according to the invention are compounds of formula (Ib) wherein $R^8$ is optionally substituted triazolyl.

Specific compounds within the scope of the present invention include: (2s,3S)3-(1-(3,5-bis(trifluoromethyl) phenyl)ethyloxy)-2-phenylpiperdine; and salts and prodrugs thereof.

For use in medicine, the salts of the compounds of formula (I) will be pharmaceutically acceptable salts. Other salts (such as the dibenzoyltartrate salts) may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, oxalic acid, fumaric acid, maleic acid, succinic acid, acetic acid, citric acid, tartaric acid, carbonic acid, phosphoric acid or p-toluenesulphonic acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

Preferred salts of the compounds according to the invention include the hydrochloride and p-toluenesulphonic acid salts.

The invention also provides pharmaceutical compositions comprising a compound of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable; excipients as set out above. Preferably the compositions are adminsitered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as MS and ALS and other neuropathological disorders such as peripheral neuropathy, for example, diabetic or chemotherapy-indnced neuropathy, and postherpetic and other neuralgias; small cell carcinomas such as small cell lung cancer (SCLC); respiratory diseases particularly those associated with excess mucus sedretion such as chronic obstructive airways disease, bronchopneumonia, chronic bronchitis, cystic fibrosis, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; emesis, including acute, delayed and anticipatory emesis, for example, induced by chemotherapy, radiation, toxins, pregnancy, vestibular disorders, surgery, migraine and variations in intercranial pressure; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and especially migraine.

The present invention further provides a compound of formula (I) or salt or prodrug thereof for use in therapy.

According to a further or alternative aspect, the present invention provides a compound of formula (I) or a salt or prodrug thereof for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I), or a salt or prodrug thereof, or a composition comprising a compound of formula (I), or a salt or prodrug thereof.

In the treatment of the conditions associated with an excess of tachykinins, a suitable dosage level is about 0.001 to 50 mg/kg per day, in particular about 0.01 to about 25 mg/kg, such aS from about 0.05 to about 10 mg/kg per day. For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

The compounds according to the invention may be prepared by a process which comprises reacting a compound of formula (II) with a compound of formula (III):

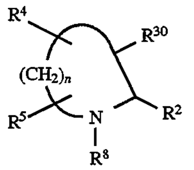

(II)

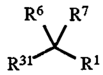

(III)

wherein $R^1$, $R^2$, $R^4$, $R^5$, $R^6$, $R^7$ and n are as defined for formula (I), $R^8$ is as defined for formula (I) except that, when $R^8$ is H it is replaced by a suitable protecting group, such as $CO_2(C_{1-6}alkyl)$; and one of $R^{30}$ and $R^{31}$ represents a leaving group and the other of $R^{30}$ and $R^{31}$ represents XH, where X is as defined for formula (I); in the presence of a base, followed by deprotection, if required.

Suitably $R^{30}$ represents XH and $R^{31}$ represents a leaving group.

Suitable leaving groups include halo, e.g. chloro, bromo or iodo, or sulphonate derivatives such as tosylate, mesylate or triflate.

The reaction is conveniently carried out in a suitable organic solvent, such as an ether, e.g. 1,2-dimethoxyethane, at a temperature in the region of 0° C. Favoured bases of use in the reaction include alkali metal amides and hydrides, such as potassium bis(trimethylsilyl)amide or potassium hydride. Suitably, potassium bis(trimethylsilyl)amide is used.

Alternatively, compounds of formula (I) may be prepared from different compounds of formula (I) by interconversion processes. In particular, interconversion processes may be used to vary the group $R^8$. For example, compounds of formula (I) wherein $R^8$ is other than H may be prepared from the corresponding compounds of formula (I) wherein $R^8$ is H by reaction with a reagent suitable to introduce the group $R^8$, for example, a halide or acyl halide, or corresponding mesylate or tosylate, of formula $R^8$-L, where L represents halo, such as chloro, bromo or iodo, methylsulphonate or p-toluenesulphonate,or any other suitable leaving group, in the presence of a base. Suitable bases of use in the reaction include inorganic bases such as alkali metal carbonates, for example, potassium carbonate. Conveniently the reaction is effected in a suitable organic solvent, for example, dimethylformamide.

Compounds of formula (I) wherein $R^8$ is $COR^9$ may be prepared from compounds of formula (I) wherein $R^8$ is H by, for example, reaction with an appropriate acid anhydride.

Compounds of formula (I) wherein $R^8$ is $C_{1-6}alkyl$ may be prepared from corresponding compounds of formula (I) wherein $R^8$ is $COR^9$ by reduction using, for example, borane or a borohydride such as sodium cyanoborohydride.

Compounds of formula (I) wherein $R^8$ is $C_{1-6}alkyl$ substituted by $CONR^aR^b$ may be prepared from corresponding compounds of formula (I) wherein $R^8$ is $C_{1-6}alkyl$ substituted by $CO_2R^a$ by treatment with ammonia or an amine of formula $NR^aR^b$.

Compounds of formula (I) wherein $R^8$ is $C_{1-6}alkyl$ substituted by 5-oxadiazolyl may be prepared from compounds of formula (I) wherein $R^8$ is $C_{1-6}alkyl$ substituted by $CH_2R^a$, where $R^a$ represents $C_{1-6}$alkyl, by reaction with a compound of formula (IV)

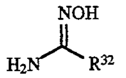
(IV)

wherein $R^{32}$ represents H or a suitable substituent, in the presence of a base.

Suitable bases of use in the reaction include alkali metals, such as, for example, sodium, and alkali metal hydrides, such as, for example, sodium hydride.

The reaction is conveniently effected in a suitable organic solvent. Which solvents will be appropriate will depend on the nature of the base used. For example, where the base used is an alkali metal, suitable solvents will include alcohols, for example, ethanol, whereas where the base used is an alkali hydride, suitable solvents will include ethers, for example, tetrahydrofuran.

Preferably the reaction is conducted at elevated temperature, such as the reflux temperature of the chosen solvent.

Compounds of formula (I) wherein $R^8$ is $C_{1-6}$alkyl substituted by tetrazolyl may be prepared from compounds of formula (I) wherein $R^8$ is $C_{1-6}$alkyl substituted by cyano by treatment with an alkali metal axide, such as sodium azide.

Compounds of formula (I) wherein $R^8$ is $C_{1-6}$alkyl substituted by thiazolyl may be prepared from compounds of formula (I) wherein $R^8$ is $C_{1-6}$alkyl substituted by $CSNH_2$ by reaction with a compound of formula Hal—$CH_2C(O)$—$R^{60}$, where Hal is halo such as bromo, chloro or iodo, and $R^{60}$ represents H or a suitable substituent.

Compounds of formula (I) wherein $R^8$ is $C_{1-6}$alkyl substituted by thioxotriazolyl may be prepared from compounds of formula (I) wherein $R^8$ is $C_{1-6}$alkyl substituted by $CONHNH_2$ by reaction with a compound of formula $R^{61}NCS$, wherein $R^{61}$ represents H or a suitable substituent such as $C_{1-6}$alkyl, in the presence of a base.

Suitable bases of use in the reaction include organic bases such as, for example, 1,8-diazabicyclo[5.4.0]undec-7-ene (DBU). The reaction is conveniently effected in a suitable orgainc solvent, such as alcohol, e.g. butanol.

Compounds of formula (I) wherein $R^8$ is $C_{1-6}$alkyl substituted by unsubstituted or substituted. triazolyl may be prepared from a compound of formula (I) wherein $R^8$ is H, by reaction with a compound of formula (V)

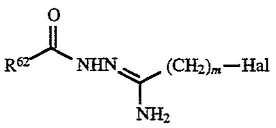
(V)

wherein Hal is as previously defined, m is 1, 2, 3, 4, 5 or 6 and $R^{62}$ is H or a group suitable as a substituent of the triazole ring, or convertable to such a group under the reaction conditions, in the presence of a base.

Suitable bases of use in the reaction include alkali metal carbonates, such as, for example, potassium carbonate.

Suitably $R^{62}$ represents H, $OCH_3$ (which is converted to an oxo substituent under the reaction conditions) or $CONH_2$.

The reaction is conveniently effected in an anhydrous organic solvent, such as, for example, anhydrous dimethylformamide, preferably at elevated temperature, such as about 60° C.

Compounds of formula (I) wherein $R^8$ represents $C_{1-6}$alkyl substituted by $CONR^aC_{1-6}$alkyl$R^{12}$ or $CONR^a$-heteroaryl may be prepared from compounds of formula (I) wherein $R^8$ is $C_{1-6}$alkyl substituted by $CO_2H$ by reaction with an amine of formula $HNR^aC_{1-6}$alkyl$R^{12}$ or $HNR^a$heteroaryl.

The intermediates of formula (II) above wherein $R^{30}$ is SH may be prepared from the corresponding intermediates of formula (II) wherein $R^{30}$ represents OH by treating the latter compound with Lawesson's reagent or phosphorus pentasulphide in a suitable solvent, e.g. pyridine, at ambient or elevated temperatures, suitably at reflux temperature.

Intermediates of formula (II) above wherein $R^{30}$ is OH may be prepared from corresponding compounds of formula (VI):

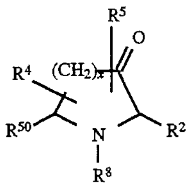
(VI)

wherein $R^2$, $R^4$, $R^5$ and $R^8$ are as defined for formula (II) above, x is 1 or 2 and $R^{50}$ is an optional carbonyl group, by reduction. Suitable reducing agents will be readily apparent to one skilled in the art and include, for example, metallic hydrides, such as lithium aluminium hydride or, preferably, sodium borohydride.

Intermediates of formula (II) wherein $R^{30}$ is a leaving group may be prepared from compounds of formula (II) wherein $R^{30}$ is OH, for example, by reaction with a thionyl halide, a mesyl halide or a tosyl halide.

Where they are not commercially available, the intermediates of formula (III) above may be prepared by the procedures described in the accompanying Examples or by alternative procedures which will be readily apparent to one skilled in the art.

Compounds of formula (VI) wherein x is 1, the carbonyl group $R^{50}$ is absent, and $R^5$ represents $CO_2(C_{1-6}$alkyl), may be prepared by reaction of compounds of formula (VII) with compounds of formula (VIII):

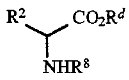
(VII)

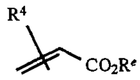
(VIII)

wherein $R^2$ is as above defined, $R^d$ represents $C_{1-6}$alkyl and $CO_2R^e$ is $R^5$; in in the presence of a base.

Suitable bases include alkali metal hydrides, such as sodium hydride, and alkali metal alkoxides, such as sodium butoxide. The reaction is conveniently effected in a suitable organic solvent, such as a hydrocarbon, for example, benzene or toluene, or an ether, for example tetrahydrofuran.

Compounds of formula (VI) wherein $R^{50}$ is absent and $R^5$ represents $CO_2(C_{1-6}$alkyl) (VIB), may be prepared by reaction of a compound of formula (VII) with a compound of formula (VIIIA)

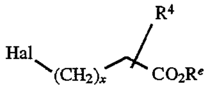
(VIIIA)

wherein x is 1 or 2 and Hal represents halo, such as chloro, bromo or iodo, and $CO_2^{Re}$ is as above defined, in the presence of a base, as above described.

Further procedures for the preparation of compounds of formula (VI) using the Dieckmann reaction will be apparent to those skilled in the art and are described in the accompanying examples.

Compounds of formula (VI) wherein $R^5$ is other than $CO_2(C_{1-6}$alkyl) may be prepared from compounds of formula (VI) wherein $R^5$ represents $CO_2(C_{1-6}alkyl)$ by decarboxylation using, for example, oxalic acid.

Alternatively, compounds of formula (VI) wherein x is 2 may be prepared from enamines of formula (IX):

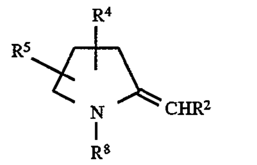

(IX)

according to the method of Cervinka et al, Collect. Czech. Chem. Commun., 1988, 53, 308–10.

Compounds of formula (VI) wherein x is 2 and the carbonyl group $R^{50}$ is present may be prepared from intermediates of formula (X):

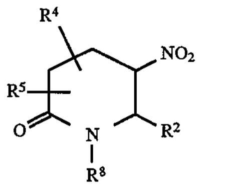

(X)

by ozonolysis, or by means of the Nef reaction. Suitable reagents and conditions are described in Organic Reactions, 38, 655.

Compounds of formula (VI) wherein one or both of $R^4$ and $R^5$ represents halo, $C_{1-6}$alkyl, $CONR^{10R11}$ or $CO_2R^{10}$ may be prepared from appropriately substituted analogues of the compounds of formulae (VII), (VIII) and (VIIIA), or by appropriate interconversion procedures which will be readily apparent to those skilled in the art.

Intermediates of formula (VII) wherein $R^d$ is $C_{1-6}$alkyl (VIIA) may be prepared from the corresponding compounds of formula (VII) wherein $R^d$ is H (VIIB), by conventional methods.

Intermediates of formula (VIIB) may be prepared from the compound of formula (XI):

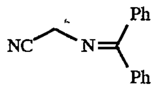

(XI)

by reaction witff a compound $R^2$-Hal, wherein $R^2$ is as above defined and Hal is halo, such as bromo, chloro or iodo, in the presence of a base, followed by hydrolysis and suitable modification of the nitrogen substituent using conventional methods.

Suitable bases of use in the reaction include metal hydroxides, for example, sodium hydroxide. The reaction is conveniently effected in a mixture of water and a suitable organic solvent, such as a hydrocarbon, for example, toluene, in the presence of a phase transfer catalyst, such as benzyltrimethylammonium chloride.

Hydrolysis is conveniently effected by heating a solution of the product of reaction between the compound of formula (X) and $R^2$-Hal in concentrated hydrochloric acid, at reflux.

The compound of formula (XI) is commercially available.

Intermediates of formula (X) are prepared as described in European Patent Application No. 0 436 334.

Compounds of formula $R^2$-Hal may be prepared according to the procedure described by E. J. Corey, Tetrahedron Lett., 1972, 4339.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. For example, intermediate alcohols of formula (II), wherein $R^{30}$ is OH, may be resolved into their component enantiomers by standard techniques, such as the formation of diastereomeric esters or amides, followed by chromatographic separation or separation by fractional crystallization and removal of the chiral auxiliary. The diastereomeric alcohols can then be used to prepare optically pure compounds of formula (I).

During any of the above synthetic sequences it may be necessary and/or desirable to protect sensitive or reactive groups on any of the molecules concerned. This may be achieved by means of conventional protecting groups, such as those described in *Protective Groups in Organic Chemistry,* ed. J. F. W. McOmie, Plenum Press, 1973; and T. W. Greene and P. G. M. Wuts, *Protective Groups in Organic Synthesis,* John Wiley & Sons, 1991. The protecting groups may be removed at a convenient subsequent stage using methods known from the art.

The exemplified compounds of this invention were tested by the methods set out at pages 36 to 39 of International patent specification No. WO 93/01165. The compounds were found to be active with $IC_{50}$nM at the NK1 receptor of less than 150 nM.

The compounds of this invention may be formulated as specifically illustrated at pages 35 to 36 of International patent specification No. WO 93/01165.

The following Examples illustrate the preparation of compounds according to the invention.

EXAMPLE 1

(2S,3S) 3-(1-(3,5-Bis(trifiuoromethyl)phenyl)ethyl) oxy)-2-phenylpiperidine hydrochloride salt a) trans-3-Nitro-6-oxo-2-phenylpiperidine Methyl 4-nitrobutyrate (1) (240 g, 1.63 mol), benzaldehyde (189 g, 1.78 mol), ammonium acetate (164 g, 2.12 mol) and ethanol (1680 ml) were placed in a 3-liter 3-necked flask equipped with a mechanical stirrer, under an atmosphere of nitrogen. The mixture was heated under reflux for four hours to yield an orange solution which crystallised on cooling. The crystalline product was isolated by filtration, washed with ethanol, ether and then dried under vacuum to afford trans-3nitro-6-oxo-2-phenylpiperidine 304 g (85%): m.p. 174°–175° C.; $^1$H NMR (360 MHz, $CDCl_3$) δ2.28–2.38 (1H, m; C$\underline{H}$H), 2.51–2.71 (3H, m, $C\underline{H}_2$+CH$\underline{H}$), 4.69–4.74 (1H, m, C$\underline{H}$$NO_2$), 5.25 (1H, d, J=6.0 Hz, PhC$\underline{H}$N), 6.0 (1H, brs, NH), 7.31–7.35 (2H, m, ArH), 7.38–7.45 (3H, m, ArH); $^{13}$C NMR ($CDCl_3$/DMSO), 22.92 ($CH_2$), 27.62 ($CH_2$), 58.58 (Ph$\underline{C}$HN), 85.01 ($CNO_2$), 126.47 (Ar), 129.02 (Ar), 129.17 (Ar), 137.85 (Ar), 169.55 (C═O); Calculated for $C_{11}H_{12}N_2O_3$; C, 59.99; H, 5.49; N, 12.72. Found: C, 60.07; H, 5.60; N, 12.76%.

b) 2,5-Dioxo-6-phenylpiperidine

Method 1 trans-3 -Nitro-6-oxo-2-phenylpiperidine (80 g, 0.364 mol) was suspended in methanol:dichloromethane (Example 1a, 1:1, 500 ml) under nitrogen. The suspension was cooled to 0° C. and potassium t-butoxide (44.8 g, 0.4 mol) was added in portions over 30 mins. The cooling bath was then removed and the solution stirred for a further 15 mins to afford a clear yellow solution. The solution was then cooled to −78° C. and ozone bubbled through the reaction mixture for 4.5 hrs, the flow of ozone was then stopped and the mixture purged with a stream of nitrogen. Anhydrous dimethyl sulphide (53 ml, 0.73 mol) was then added dropwise and the reaction mixture allowed to warm to room temperature. The solvent was then removed at reduced pressure and the residual orange solid dissolved in dichloromethane (800 ml), washed with water (2×200 ml), dried ($MgSO_4$), the solvent was then removed at reduced pressure. The residue was suspended in ether, filtered, and the pale yellow crystalline solid washed with ether (3×100ml) and dried under vacuum to afford 2,5-dioxo-6-phenylpiperidine (54 g, 78%): m.p. 160°–164° C.; $^1$H NMR (360 MHz, DMSO-$d_6$) δ2.55–2.58 (2H, m, C$\underline{H}_2$), 2.63–2.70 (2H, m, C$\underline{H}_2$), 2.5–2.9 (4H, m, C$\underline{H}_2$C$\underline{H}_2$), 4.96 (1H, d, J=2.4 Hz, PhC$\underline{H}$), 7.4–7.7 (5H, m, Ar), 8.2 (1H, brs, NH); m/z ($CI^+$) 207 (M+$NH_4$+), 190 (M+H); Calculated for $C_{11}H_{11}NO_2$ C; 69.83; H, 5.86; N, 7.40%. Found C, 70.04; H, 5.77; N, 7.60%.

Method 2

To a 5L flask containing ammonium acetate (450g) which had been thoroughly purged with nitrogen was added a freshly prepared solution of titanium trichloride (300 g, 1.95 mol) in deoxygenated water (2.1L) with ice-bath cooling. To the resulting green solution was added a solution of trans-3-nitro-6-oxo-2-phenylpiperidine (Example 1a, 90 g, 0.409 mol) and sodium methoxide (27 g, 0.5 mol) in methanol (750 ml). The solution was stirred for 1 hr at 0° C. and for a further 1 hr at room temperature. Concentrated hydrochloric acid (240 ml) was added dropwise, and the resulting mixture extracted with ethyl acetate (1000 ml, 3×500 ml). The combined organic extracts were washed with saturated brine (1000 ml), dried ($MgSO_4$), and evaporated under reduced pressure. The residue was suspended in ether and filtered and the pale yellow crystalline solid was washed with ether (3×100 ml) and dried in vacuo to afford 2,5-dioxo-6-phenylpiperidine (58 g, 75%): m.p. 160°–164° C.

c) (±)-cis-3-Hydroxy-2-phenylpiperidine 4-toluenesulphonate salt

Sodium borohydride (3.8 g, 0.1 mol) was added portionwise to a cooled (–10° C.) stirred suspension of 2,5-dioxo-6-phenylpiperidine (38 g, 0.2mol) in methanol (600 mol), and stirring was continued for a further 30 mins. The solvent was removed under reduced pressure, the residue was then azeotroped with toluene (2×150 ml). To the residue was added $BH_3$.THF (317 ml of a 1M soln in THF, 0.317 mol) and the colourless solution heated at reflux for 16hr, then coiled to 0° C. Excess borane was quenched by the cautious addition of methanol (50 ml), and the solvent was then removed under reduced pressure. The residue was dissolved in ethanol (300 ml), anhydrous $K_2CO_3$ (21 g, 0.15 mol) was added and the mixture heated at reflux for 7 hr. After cooling to room temperature the solvent was removed at reduced pressure and the residue dissolved in water (200 ml) and extracted with dichloromethane (4×250 ml). The combined organic extracts were then washed with brine (150 ml), dried ($MgSO_4$) and concetrated under reduced pressure to afford the crude hydroxy amine (21 g) as a crystalline white solid, consisting of a 11:1 mixture of cis/trans isomers.

This crude material was dissolved in methanol (290 ml) and 4-toluenesulphonic add (38 g, 0.3 mol) added. The precipitated solid was recrystallised from methanol to yield (+)-cis-3-hydroxy-2-phenylpiperidine4-toluenesulphonate salt (56.7 g, 81%) as a white crystalline solid: m.p. 266°–271° C.; $^1$H NMR (360 MHz, DMSO-$d_6$) δ1.66 (1H, m,), 1.64 (2H, m, ), 2.02 (1H, m,) 2.29 (3H, s, Me), 3.06 (1H, dr, J=3.01, 12.9 Hz, NC$\underline{HH}$), 3.26 (1H, dd, J=12.9 Hz, NCH$\underline{H}$), 3.96 (1H, bs, C$\underline{H}$OH), 4.35 (1H, s, OH), 5.40 (1H, d, J=3.9, NC$\underline{H}$Ph), 7.10 (2H, d, J=7.9 Hz, Tosylate ArH), 7.34–7.42 (5H, m, Ph), 7.46 (2H, d, J=7.9 Hz, Tosylate ArH); Calculated for $C_{18}H_{23}NO_4S$ C, 61.87; H, 6.63; N, 4.01. Found C, 61.65; H, 6.63; N, 4.02.

d) (2S,3S)-3-Hydroxy-2-phenylyiperidinium(–)-dibenzoyl tartrate salt (±)-cis-3-Hydroxy-2-phenylpiperidine 4-toluenesulphonate salt (Example 1c, 218.5 g, 0.626 mol) was dissolved in a mixture of dichloromethane (2500 ml), methanol (250 ml) and 10% aqueous sodium carbonate solution (1400 ml). The organic phase was separated and washed with 10% aqueous sodium carbonate solution (500 ml) followed by brine (saturated, 500 ml) after drying ($K_2CO_3$), the solvent was removed at reduced pressure to afford the free base (106 g).

The free base (106.4 g, 0.60 mol) was dissolved in methanol (250 ml) and a solution of (–) dibenzoyl tartaric acid (59.2 g, 0.165 mol) in methanol (250 ml) added. The solution was cooled to 0° C. and the precipitate isolated by filtration to yield (2S, 8S)-3-hydroxy-2-phenylipperidinium (–)-dibenzoyltartrate salt (59.31 g) (ee>98%, HPLC*). The mother liquors were dissolved in 10% aqueous sodium carbonate solution (1000 ml) and extracted with dichloromethane (1000 ml), dried ($K_2CO_3$) and evaporated to afford the free residual free base (77 g). This was dissolved in methanol (200 ml) and a solution of (+) dibenzoyl tartaric acid (59.2 g, 0.165 mol) in methanol (150 ml) added. Cooling and filtration afforded (2R, 3R)-3-hydroxy-2-phenylpiperidinium (+)-dibenzoyltartrate salt (82.6 g) (ee 97.3%, HPLC*). The mother liquors were again recycled to give a second crop of (2S, 3S)-3-hydroxy-2-phenylpiperidinium (–)-dibenzoyltratrate salt 34.3 g) (ee 97.6%, HPLC*). The combined crops of(2S, 3S)-3-hydroxy-2-phenylpiperidinium (–)-dibenzoyltartrate salt were recrystallised from aqueous ethanol (500 ml) to yield (2S, 3S)-3-hydroxy2-phenylpiperidiumium (–)-dibenzoyltartrate salt (84.53, 75.7% of available enantiomer) (ee>99.5%, HPLC*): m.p. 221°–222° C.: Calculated for $C_{2O}H_{22}NO_5$ C, 67.40; H, 6.22; N, 3.93%. Found C, 67.34; H, 6.23; N, 4.00%.

HPLC* ChiraI HPLC determination: ULTRON $^R$ ES-OVM Column (150 mm ×4.6 mm id, 5 vm) 0.5% Ethanol in 10 mM K2HP$O_4$ (pH 7.5) at 1.5 ml/min, OD 210 nM.

e) (2S,3S)-1-t-Butyloxycarbonyl-3-hydroxy-2-phenyl piperidine (2S,3S)-3-Hydroxy-2-phenylpiperidinium (–)-dibenzoyl tartrate salt (71.6 g, 0.20 mol) was dissolved in dichloromethane (1000 ml) at 35° C., and a solution of sodium carbonate (41 g, 0.39 mol) in water (200 ml) was added and the mixture was heated (stem bath) until all the solid had dissolved (a small amount of methanol was added to aid dissolution). The organic phase was separated and the aqueous phase extracted with dichloromethane (2×300 ml). The combined organic phases were wished with aqueous sodium carbonate (2×100 ml, saturated), dried ($K_2CO_3$) and concentrated at reduced pressure to afford (2S, 3S)-3-hydroxy-2-phenylpiperidine (35 g, 100%) as a white crystalline solid, m.p. 93°–95° C.; $[\alpha]_D$=+98.5 (c=1, methanol).

This aminoalcohol (34 g, 0.19 mol) was dissolved in anhydrous dichloromethane (500 ml) under a nitrogen atmosphere, and di-t-butyl dicarbonate (44 g, 0.20 mol) was added portionwise with stirring. The reaction mixture was then stirred at room temperature for 18 hr, before the solvent was then removed at reduced pressure and the residue crystallised from hexane to afford (2S,3S)-1-t-butyloxycarbonyl-3-hydroxy-2-phenylpiperidine (50 g, 100%) mp=66°–67° C.: $^1$H NMR (360 MHz, $CDCl_3$) 1.46

(9H, s, t-Bu), 1.66–1.88 (4H, m, 2×$CH_2$), 3.1 (1H, ddd, J=2.8, 12.6, 12.6 Hz, CHHN), 3.92–4.12 (2H, m, CHOH, CHHN), 5.43 (H, d, J=5.6 Hz, NCHPh), 7.34–7.47 (3H, m, AR), 7.40–7.55 (2H, m, Ar).

f) 1-(3,5bis(trifiuoromethyl)phenyl)-1-hydroxyethane

Method A

To a cooled (–20° C.) solution of 3,5-bis(trifiuoromethyl) benzaldehyde (11.0 g) in anhydrous diethyl ether (30 ml) was added a solution of methylmagnesium bromide (20 ml, 3M in diethyl ether). After stirring the solution at –20° C. for 15 minutes and at ambient temperature for 30 minutes, water was added dropwise. Ethyl acetate and Saturated $NH_4Cl$ were added and the organic phase washed with saturated brine and dried ($MgSO_4$). Removal of the solvent in vacuo and recrystallisation from hot hexane gavel-(3,5-bis (trifiuoromethyl)phenyl)-1-hydroxyethane, 9.0 g.

Method B

To a solution of 3,5-bis(trifluoromethyl)aeetophenone (18.4 g) in methanol (40 ml) was slowly added sodium borehydride (2.72 g) with cooling in a water bath at 20° C. After 30 minutes ethyl acetate (200 ml) and saturated $NH_4Cl$ (50ml) were added and the organic phase washed with water (twice 50 ml), saturated brine and dried ($MgSO_4$). Evaporation and recrystallisation from hot hexane gave 1-(3,5-bis (trifluoromethyl)phenyl)-1-hydroxyethane 17.4 g $^1$H NMR (250MHz, $CDCl_3$) δ7.84 (2H; s; 2,6-arylH), 7.79 (1H; s; 4-arylH), 5.03 (2H; q, J=6.5 Hz; $CH_3$CH), 1.54 (3H; d, J=6.5 Hz; $CH_3$).

g) 1-(3,5-bis(trifluoromethyl)phenyl)-1-bromoethane

To 1-(3,5-bis(trifiuoromethyl)phenyl)-1-hydroxyethane (10 g) was added phosphorous tribromide (3.7 ml) to give a clear solution. After 30 minutes the solution was added to water (300 ml) and the solution stirred for a further 30 minutes. Petroleum ether bp=60°–80° C. was added and the organic solution washed with water (×3), saturated, $NaHCO_3$, saturated brine and dried ($MgSO_4$). The solution was evaporated in vacuo and the residue distilled $b_{1-4\ mm}$=69° C. to give 1-(3,5-bis(trifluoromethyl)phenyl)-1-bromoethane- $^1$H NMR (250 MHz; $CDCl_3$) δ7.88 (2H; s; 2,6-arylH), 7.80 (1H; s; 4-arylH), 5.23 (2H,; q, J =6.9 Hz; $CH_3$CH), 2.09 (3H; d, J =6.9 Hz; $CH_3$).

h) (2S,3S) 3-(1-(3,5-bis(trifluoromethyl)phenyl)ethyloxy) -N-t-butoxycarbonyl-2-phenylpiperidine A solution of (28,38) 1-t-butoxycarbonyl-3-hydroxy-2-phenylpiperidine (Example 1e, 0.51 g) and sodium hydride (80% suspension in oil (0.084 g) in tetrahydrofuran (5 ml) and N,N-dimethylformamide (1 ml) was sonicated in a water bath under an atmosphere of nitrogen for 30 minutes followed by addition of 1-(3,5-bis(trifhoromethyl))-1-bromoethane (Example 1g, 1.19 g). After stirring the solution for 2h a further addition of sodium hydride (0.084 g) and 1-(3,5-bis(trifluoromethyl)-1-bromoethane was made. After an additional 1h, water was carefully added followed by ethyl acetate and the organic phase washed with water (×3), saturated brine and dried ($MgSO_4$). After removal of the solvent in vacuo the residual oil was chromatographed on silica gel eluting successively with 0, 5%, 10% ethyl acetate in hexane to give (2S,3S) 3-(1-(3,5-bis (trifluoromethyl)phenyl ethyloxy)-N-t-butoxycarbonyl-2-phenylpiperidine as two separate diastereomers.

i) (2S,3S) 3-(1-(3,5-bis(trifluoromethyl)phenyl)ethyloxy) -2-phenylpiperidine hydrochloride salt The individual diastereomers of the N-t-butoxycarbonyl derivative (Example 1b, 222.5mg) were treated with 2M HCl in methanol (5 ml) for 2.5h. The solution was evaporated to dryness and on addition of diethyl ether the resultant solid was removed by filtration.

Diastereomer A mp=256°–263° C., $^1$H NMR (DMSO$d_6$, 360 MHz) δ8.04 (2H; s; 2,6-arylH), 8.00 (1H; s; 4-aryl H), 7.55–7.40 (5H; m; aryl), 4.5 (2H; m), 3.96 (1H; s), 3.06 (1H; t), 1.7 (3H; m), 1.60 (1H; bd), 0.89 (3H; d, J=6.4 Hz, $CH_3$).

Diastereomer B (after chromatography in chloroform: acetic acid: methanol 85:5:10, evaporation and hydrochloride salt formation) mp=302°–312° C.; m/z CI+=418(M+H), CI–=416(M-H). $^1$H NMR (DMSO$d_6$, 360 MHz) δ7.86 (1H; s; 4-aryl1H), 7.49 (2H; s; 2,6-arylH), 7.36–7.30 (1H; m; aryl), 4.76 (1H; q; J=6.28 Hz; $CH_3$CH), 4.42 (1H; s), 3.60 (1H; s), 3.06 (1H; t), 2.28 (1H; d), 2.01 (1H; m), 1.72 (2H; m), 1.38 (3H; d, J=6.4 Hz; $CH_3$).

EXAMPLE 2

5-[( 2S,3S R)3-[1-(3,5-Bis(trifluoromethyl)phenyl)ethoxyl]2-phenylpiperidin-1-ylmethyl]-2.4-dihydro-[1,2,4]triazol-3-one a) To a cooled (0° C.) solution of chloroacetonitrile (54.1 g) in methanol (100 ml) was added dropwise a solution of 1M-sodium mothoxide (20 ml). After stirring the solution at 0° C. for 30 mins glacial acetic acid (1.2 ml) was added followed by a solution of methyl carbazate (64.5 g, fleshly distilled in vacuo) in warmed dimethyl formamide (35 ml) and methanol (300 ml). After stirring the solution at 0° C. for 30 minutes the crystalline solid which had formed was removed by filtration and washed with ethyl acetate to give N-carbomethoxy-2-chloroacetamidrazone, mp=138°–140° C.

b) To a solution of diastereomer B (Example 1i, 2.0 g)in dimethylformamide (10 ml) was added $K_2CO3$ (3.04 g) and N-carbomethoxy-2-chloroacetamidrazone (Example 2a, 0.876 g). The solution heated at 80° C. for 1h then partitioned between ethyl acetate and water. The organic phase was washed with water and saturated brine and dried ($MgSO_4$). Upon removal of the solvent in vacuo the residual foam was dissolved in xylene (40 ml) and the solution heated to 140° C. for 6h. The solution was evaporated and the residue purified by col-ran chromatography on silica gel eluting with 0% and 4% methanol in dichloromethane to give the title compound. mp=214°–215° C. m/z (CI+)=515 (M+H).

EXAMPLE 3

5-[(2S,3S,R)-3-[1-(3,5-Bis(trifiuoromethyl)phenyl)ethoxy]-2-phenylpiperidin-1-ylmethyl]-[1.2.4]triazole a) To a cooled (0° C.) solution of chloroacetonitrile (10 g) in methanol (8 ml) was added 1M-sodium methoxide (3.4 ml). After 30 minutes at 0° C. glacial acetic acid (0.22 ml) was added followed by dropwise addition of a solution offorrnle acid hydrazide (7.9 g) in warmed methanol (30 ml). After the solution had been stirred at 0° C. for 15 minutes ethyl acetate (30 ml) were added. After 30 minutes at 0° C. the crystalline solid which had formed was removed by filtration and washed with ethyl acetate and diethyl ether to give N-formyl-2-chloroacetamidohydrazone mp=119°–120° C.

b) To a solution ofdiastereomer B (Example 1i, 0.4 g) in dimethylforrnamide (2 ml) was added $K_2CO_3$ (0.68 g) and N-formyl-2-chloroacetamidohydrazone (Example 2a). The solution was stirred at room temperature for 2h then at 100° C. for 2h. The solution was cooled and the residue purified by chromatography on silica gel (eluting with 4% methanol/dichloromethane) to give the title compound mp=182°–183° C.

EXAMPLE 4

5-[1-[(2S,3S,R)-3-[1-(3,5-bis(trifluoro-methyl)phenyl)ethoxy]-2-phenylpiperidin-1-yl]ethyl]-2,4-dihydro -[1,2,4]triazol-3-one a) To a cooled (0° C.) solution of α-chloropropionitrile (5.9 g) was added 0.3M-sodium methoxide (6 ml). After stirring the solution for 0.75h glacial acetic acid (0.11ml) was added followed by a solution of methyl carbazate (5.2 g, freshly distilled in vacuo) in warmed dimethyl formamide (8 ml). After stirring the solution at 0° C. for 0.5h the solution was evaporated to a small volume and diethyl ether (50 ml) added. The crystalline solid was removed by filtration and washed with diethyl ether to give N-carbomethoxy-2-chloropropionamidrazone.

b) To a solution of diastereomer B (Example 1i, 0.096 g) in dimethylformamide (2 ml) was added $K_2CO_3$ (0.146 g) and N-carbomethoxy-2-chloropropionamidrazone (0.046 g, Example 4a). The solution was stirred at 100° C. for 2h and 140° C. for 2h. The cooled solution was chromatographed on silica gel (eluting with 4% methanol/dichloromethane). The product was crystallized from diethyl ether to give the title compound mp=257°–258° C.

EXAMPLE 5

(2S,3S)-3-(1(3,5-Dichlorophenyl)ethyloxy)-2-phenylpiperidine hydrochloride.

The title compound was prepared by a method analogous to that described in Example 1. mp>250° C.

EXAMPLE 6

5-[(2S,3S,R)-3-[1-(3,5-Dichlorophenyl)ethyloxy]-2-phenylpiperidin-1-ylmethyl]-2,4-dihydro][1,2,4]-triazol-3-one.

The title compound was prepared from the product of Example 5 by a procedure analogous to that described in Example 2. m/z (CI+)=447, 449. Mp 191°–192° C.

EXAMPLE 7

(2S,3S)-3-(1-(Phenyl)ethyloxy)-2-phenylnpiperidine hydrochloride

The title compound was prepared by an analogous procedure to that described in Example 1, mp=259°–268° C.

EXAMPLE 8

5-[(2S,3S,R)-3-[1-(Phenyl)ethyloxy]-2-phenylpiperidin-1-ylmethyl]-2,4-dihydro-[1,2,4]-triazol-3-one The title compound was prepared from the product of Example 7 by a procedure analogous to that described in Example 2. Mp =211°–213° C.

EXAMPLE 9

(2S,3S)-3-(1-(3-Chlorophenyl)ethyloxy)-2-phenylpiperidine hydrochloride

The title compound was prepared by a method analogous to that described in Example 1. Mp =273°–276° C.

EXAMPLE 10

5-[(2S,3S,R)-3-[1-(3-Chlorophenyl)ethyloxy)-2-phenylpiperidin-1-ylmethyl]-2,4-dihydro-[1,2,4] triazol-3-one The title compound was prepared from the product of Example 9 by a procedure analogous to that described in Example 2. Mp=164°–165° C.

EXAMPLE 11

2S,3S)-3-(1-(3-isopropoxyphenyl)ethyloxy]-2-phenylpiperidine hydrochloride

The title compound was prepared by a method analogous to that described in Example 1, Mp=253°–256° C.

EXAMPLE 12

5-[(2S,3S,R)-3-[1-[3-Isopropoxphenyl)ethyloxy]-2-phenylpiperidin-1-1methyl]-2,4-dihydro-[1,2,4] triazol-3-one The title compound was prepared from the product of Example 11 by a procedure analogous to that described in Example 2. Mp=104°–106° C.

EXAMPLE 13

(2S,3S)-3-(1-(3,5-Bis(trifiuoromethyl)ohenyl) ethyloxy)-2-(4-fluorophenyl)piperidine hydrochloride The title compound was prepared by a procedure analogous to that described in Example 1 using 4-fluorobenzaldehyde to give diastereomer B: mp=265°–266° C.

EXAMPLE 14

5-[(2S,3S,R)-3-[1 -(3,5-Bis(trifiuoromethyl)phenyl) ethoxy]-2-[4-fluorophenyl)pineridin-1-ylmethyl]-2, 4-dihydro-[1,2,4]triazo]-3-one The title compound was prepared from the product of Example 13 by a procedure analogous to Example 2. Mp=222°–223° C.

EXAMPLE 15

5-[2S,3S,R)-3-[1 -(3,5-Bis(trifluoromethyl)phenyl) ethoxy]-2-(4-fluorophenyl)piperidin-1-ylmethyl]-[1, 2,4]triazole The title compound was prepared from the product of Example 13 by a procedure analogous to Example 3. mp=175°–177° C.

EXAMPLE 16

5-[(2S,3S,R),3-(3-Chloro-5-t-butyl)phenyl) ethyloxyl-2-(4-fluorophenyl)piperidin-1-ylmethyl]-2,4-dihydro-[1,2,4]triazol-3-one The title compound was prepared from (2S,3S)-1-t-butyloxycarbonyl-3-hydroxy-2-(4-fluorophenyl)piperidine (prepared as intermediate in Example 13) using procedures analogous to those described in Examples 1h, 1i, 2. Mp=213° C.

EXAMPLE 17

(2S, 3S,R)-3-(1-(3-Trifluoromethylphenyl)ethyloxy)-2-phenylpiperidine hydrochloride The title compound was prepared by a method analogous to that described in Example 1, m/z (CI+)=850 (M+H).

EXAMPLE 18

5-[(2S,3S,R)-3-[1-(3-Trifluoromethylphenyl)ethyloxy]2-phenylpiperidin-1-ylmethyl]-2,4-dihydro-[1,2,4]triazol-3-one The title compound was prepared from fie product of Example 17 by a procedure analogous to that described in Example 2. Mp=143°–145°C.

EXAMPLE 19

[2S,3S,R)-3-(1-[3-Bromophenyl)ethyloxy)-2-phenylpiperidine hydrochloride

The title compound was prepared by a method analogous to that described in Example 1. Mp=267°–268° C.

EXAMPLE 20

5-[(2S,3S,R)-3-[1-(3-Bromophenyl)ethyloxy]-2-phenylpiperidin-1-ylmethyl]-2,4-dihydro-[1,2,4]triazol-3-one The title compound was prepared from the product of Example 19 by a procedure analogous to that described in Example 2. Mp=165° C.

EXAMPLE 21

(2S,3S,R)-3-[1-(2-Chloro-5-trifluoromethylphenyl)ethyloxyl]-2-(4-fluorophenyl)piperidine hydrochloride The title compound was prepared from (2S,3S)-1-t-butyloxycarbonyl-3-hydroxy-2-(4-fluorophenyl)piperidine (prepared as intermediate in Example 13) using procedures analogous to those described in Examples 1h, 1i. Mp=272°–273° C.

EXAMPLE 22

5 -[2S,3S,R)-3-[-(2-Chloro-5-trifluoromethylyphenyl)ethyl[oxy]-2-(4-fluoroyhenyl)piperidin-1-ylmethyl]-2,4-dihydro-[1.2.4]triazol-3-one The title compound was prepared from the product of Example 21 by a procedure analogous to that described in Example 2. Mp=208°–209° C.

We claim:

1. A compound of formula (I), or a salt thereof:

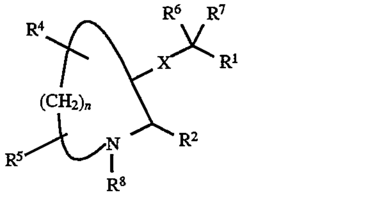

(I)

wherein n is 3 and where any carbon atom of $(CH_2)_n$ may be substituted by $R^4$ and/or $R^5$;

X represents O or S;

$R^1$ represents $(CH_2)_q$phenyl, wherein q is 0, 1, 2 or 3, which may be optionally substituted in the phenyl ring by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, —$OR^a$, $SR^a$, $SOR^a$, $SO_2R^a$, —$NR^aR^b$, —$NR^aCOR^b$, —$NR^aCO_2R^b$, —$CO_2R^a$and —$CONR^aR^b$;

$R^2$ represents aryl selected from phenyl and naphthyl; heteroaryl selected from indazolyl, thienyl, furyl, pyridyl, thiazolyl, tetrazolyl and quinolyl; moiety may be substituted by $C_{1-6}$alkyl, $C_{1-6}$alkoxy halo benzhydryl; or benzyl; wherein each aryl or heteroaryl or trifluoromethyl;

$R^4$ and $R^5$ each independently represent H, halo, $C_{1-6}$alkyl, $CO_2{}^{Ra}$or $CONR^aR^b$or $R^4$ and $R^5$ together form an oxo;

$R^6$ represents H or $C_{1-6}$alkyl;

$R^7$ represents $C_{1-6}$alkyl or phenyl optionally substituted by 1, 2 or 3 groups selected from $C_{1-6}$alkyl, $C_{2-6}$alkenyl, $C_{2-6}$alkynyl, halo, cyano, nitro, trifluoromethyl, trimethylsilyl, —$OR^a$, $SR^a$, $SOR^a$, $SO_2R^a$, $NR^aR^b$, —$NR^aCOR^b$, —$NR^aCO_2R^b$, —$CO_2R^a$ and —$CONR^aR^b$;

$R^8$ represents H, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, cyano, $COR^a$, $NR^aR^b$, $C(NOH)NR^aR^b$, CONHphenyl ($C_{1-4}$alkyl), $COCO_2{}^{Ra}$, $CONRHNR^aR^b$, $C(S)NR^aR^b$, $CONR^aC_{1-6}alkylR^{12}$, $CONR^{13}C_{2-6}$alkynyl, $CONR^{13}C_{2-6}$alkenyl, $COCONR^aR^b$, $CONR^aC(NR^b)NR^aR^b$, $CONR^a$heteroaryl, wherein heteroaryl is defined above, and phenyl optionally substituted by one or more substituents selected from $C_{1-6}$alkyl, $C_{1-6}$alkoxy, halo and trifluoromethyl) or $C_{1-6}$alkyl, optionally substituted by oxo, substituted by an aromatic heterocyclic group selected from thienyl, furyl, pyrrolyl, pyridyl, pyrazolyl, triazolyl, tetrazolyl, thiazolyl, pyrazinyl, pyridazinyl, oxazolyl, oxadiazolyl, thiadiazolyl, isoxazolyl, quinolyl, isothiazolyl, imidazolyl, benzimidazolyl, benzoxazolyl, benzothiophenyl, benzofuranyl and indolyl, which group is optionally substituted by $C_{1-6}$alkyl, $C_{1-6}$alkxy, oxo, thioxo, halo, trifluoromethyl, $N^{Ra}R^b$, $NR^aCOR^b$, $CONR^aR^b$, $CO_2R^a$, $SO_2R^a$ and $CH_2OR^a$, where $R^a$ and $R^b$ are as previously defined;

$R^a$ and $R^b$ each independently represent H, $C_{1-6}$alkyl, trifluoromethyl or phenyl optionally substituted by $C_{1-6}$alkyl, halo or trifluoromethyl;

$R^{12}$ represents $OR^a$, $CONR^aR^b$ or heteroaryl; and $R^{13}$ represents H or $C_{1-6}$alkyl.

2. A compound as claimed in claim 1 of formula (Ia), or a salt thereof:

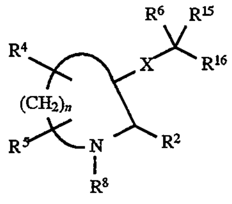

(Ia)

wherein $R^2$, $R^4$, $R^5$, $R^6$, $R^8$, X and n are as defined for formula (I) above;

$R^{15}$ represents $C_{1-6}$alkyl; and $R^{16}$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, —$OR^a$, $SR^a$, $SOR^a$, $SO^2R^a$, —$NR^aR^b$, —$NR^aCOR^b$, —$NR^aCO_2R^b$, —$CO_2R^a$and —$CONR^aR^b$.

3. A compound as claimed in claim 1 of formula (Ib) or a salt thereof:

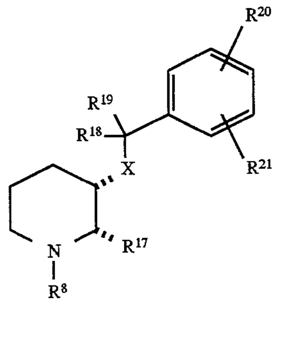
(Ib)

wherein

X represents O or S;

$R^8$ is as defined for formula (I);

$R^{17}$ represents phenyl or benzhydryl wherein any of the phenyl rings of the phenyl or benzhydryl moieties may optionally be substituted by halo or trifluoromethyl, preferably unsubstituted phenyl;

$R^{18}$ is methyl;

$R^{19}$ is H or methyl; and $R^{20}$ and $R^{21}$ independently represent H $C_{1-6}$alkyl, $C_{2-6}$alkenyl, $C_{2-6}$alkynyl, chloro, bromo, fluoro, iodo, cyano, nitro, trifluoromethyl, trimethylsilyl $OR^a$, $SR^a$, $SOR^a$, $SO_2R^a$, $NR^aR^b$, $NR^aCOR^b$, $NR^aCO_2R^b$, $CO_2R^a$, or $CONR^aR^b$, where $R^a$ and $R^b$ are as previously defined.

4. A compound as claimed in claim 1 wherein n is 3.

5. A compound as claimed in claim 1 claim wherein X is O.

6. A compound as claimed in claim 1 claim wherein q is O and $R^1$ represents phenyl substituted by one or more groups selected from methyl, trifluoromethyl, chloro and t-butyl.

7. A compound as claimed in claim 1 wherein $R^2$ represents unsubstituted benzhydryl, phenyl substituted by halo or unsubstituted phenyl.

8. A compound as claimed in claim 1 wherein $R^6$ represents H or methyl.

9. A compound as claimed in claim 1 wherein $R^7$ is methyl or ethyl.

10. A compound as claimed in claim 1 wherein $R^8$ represents $CH_2$-Het, $CH(CH_3)$-Het, $C(CH_3)_2$-Het or C(O)-Het where Het is substituted or unsubstituted oxazolyl, oxadiazolyl, tetrazolyl, thiazolyl, thiadiazolyl, furanyl, thienyl, triazolyl, pyrazinyl, pyridyl, pyridazinyl, imidazolyl or benzimidazolyl.

11. A compound selected from (2S,3S)3-(1-(3,5-bis(trifluoromethyl)phenyl)ethyloxy)-2-phenylpiperidine; or a salt or prodrug thereof.

12. A pharmaceutical composition comprising a compound as claimed in claim 1 in association with a pharmaceutically acceptable carrier.

13. A process for the preparation of a compound as claimed in claim i which process comprises reacting a compound of formula (II) with a compound of formula (III)

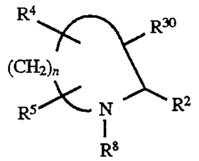
(II)

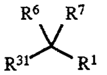
(III)

wherein one of $R^{30}$ and $R^{31}$ represents a leaving group selected from: chloro, bromo, iodo, tosylate, mesylate, and triflate; and the other of $R^{30}$ and $R^{31}$ represents XH, wherein X is as defined in claim 1; and, if necessary or desired, converting the compound of formula (I) so prepared into another compound of formula (I), or a salt or prodrug thereof.

14. A method for the treatment or prevention of physiological disorders associated with an excess of tachykinins, which method comprises administration to a patient in need thereof of a tachykinin reducing amount of a compound according to claim 1, or a salt thereof, or a composition comprising a compound according to claim 1, or a salt thereof.

15. A method according to claim 14 for the treatment or prevention of pain or inflammation.

16. A method according to claim 14 for the treatment or prevention of migraine.

17. A method according to claim 14 for the treatment or prevention of emesis.

* * * * *